United States Patent [19]

Lamont

[11] Patent Number: 5,171,535

[45] Date of Patent: Dec. 15, 1992

[54] BREATH ALCOHOL TESTER

[76] Inventor: Wayne Lamont, 222 Alta B. Crescent, Amherstburg, Ontario N9V 3R3, Canada

[21] Appl. No.: 696,729

[22] Filed: May 7, 1991

Related U.S. Application Data

[63] Continuation-in-part of Ser. No. 596,365, Oct. 12, 1990, abandoned.

[51] Int. Cl.⁵ .............................................. G01N 1/22
[52] U.S. Cl. ...................................... 422/85; 422/84; 436/132; 436/164
[58] Field of Search ........................... 422/85, 83–84; 436/132, 164

[56] References Cited

U.S. PATENT DOCUMENTS 2,867,511  1/1959  Harger ................................. 422/85

*Primary Examiner*—James C. Housel
*Assistant Examiner*—Lyle A. Alexander
*Attorney, Agent, or Firm*—Gifford, Groh, Sprinkle, Patmore and Anderson

[57] ABSTRACT

A disposable breath alcohol tester is disclosed which includes a transparent housing defining an interior chamber. A tube extends through the housing chamber so that one end of the tube is open to one side of the chamber while the second end of the tube is open exteriorly to the opposite side of the chamber. An inflatable bladder is connected to the second end of the tube. The tube contains an alcohol reactant substance which changes color whenever the alcohol content of exhaled air passing through the tube exceeds a predetermined amount and at least a portion of both the tube and the housing are transparent so that the alcohol reactant substance can be observed. In use, the person under test inflates the bladder by blowing through the tube and thus through the alcohol reactant substance. The color of the alcohol reactant substance is then observed in order to determine the alcohol content of the exhaled breath.

9 Claims, 1 Drawing Sheet

BREATH ALCOHOL TESTER

CROSS REFERENCE TO RELATED APPLICATIONS

The present application is a continuation-in-part of U.S. patent application Ser. No. 07/596,365, entitled BREATH ALCOHOL TESTER, filed on Oct. 12, 1990 now abandoned with Wayne Lamont as the inventor.

BACKGROUND OF THE INVENTION

I. Field of the Invention

The present invention relates to a breath alcohol tester.

II. Description of the Prior Art

There are many previously known breath alcohol testers which test the alcohol content in the exhaled breath of the person under test. This amount of alcohol, in turn, is related to the alcohol content of the blood of the person being tested.

These previously known breath alcohol tests have proven both effective and accurate in operation. Many of the previously known breath alcohol testers are capable of producing an accurate percentage indicative of the alcohol content of the person's blood who is undergoing the test.

One disadvantage of these previously known devices, however, is that they are very expensive both to purchase and maintain. Furthermore, in order to obtain accurate results from these previously known breath alcohol testers, it is necessary to train the person giving the test which is not only inconvenient, but also expensive.

SUMMARY OF THE PRESENT INVENTION

The present invention provides a simple breath alcohol tester which overcomes all of the above mentioned disadvantages of the previously known devices.

In brief, the breath alcohol tester of the present invention comprises a transparent housing. A tube extends through the housing so that one end of the tube is opened exteriorly to one side of the housing while the opposite end of the tube is opened exteriorly to the opposite end of the housing. An inflatable bladder has its inlet fluidly connected to the second side of the housing chamber while a one way valve permits air flow through the tube into the bladder but prevents back flow of air from the bladder through the tube.

An alcohol reactant substance is contained within the interior of the tube so that air flow through the tube also contacts the alcohol reactant substance. This alcohol reactant substance is preferably a crystalline silica gel supporting potassium dichlorate, silver nitrate and sulphuric acid.

In operation, the person under test inflates the bladder by blowing through the tube so that the exhaled breath also comes in contact with the alcohol reactant substance. The bladder thus forms a means for indicating the volume of the exhaled breath since the size of the bladder increases proportionally with the volume of the exhaled breath.

After the required amount of breath has been exhaled, the color of the alcohol reactant substance is observed which is indicative of the alcohol content of the exhaled breath.

BRIEF DESCRIPTION OF THE DRAWING

A better understanding of the present invention will be had upon reference to the following detailed description when read in conjunction with the accompanying drawing, wherein like reference characters refer to like parts throughout the several views, and in which.

DETAILED DESCRIPTION OF A PREFERRED EMBODIMENT OF THE PRESENT INVENTION

Figure 1:
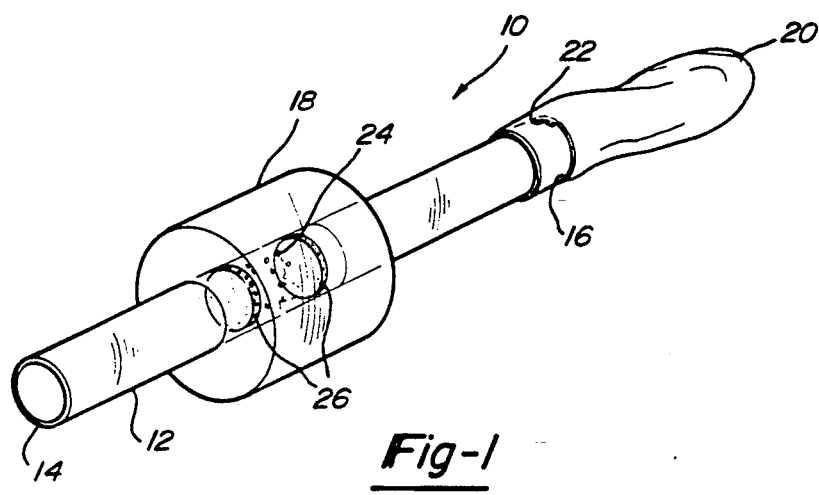
FIG. 1 is a side view illustrating a preferred embodiment of the present invention.

With reference first to FIG. 1, a preferred embodiment of the breath alcohol tester 10 of the present invention is thereshown and comprises an elongated tube 12 having a first end 14 and a second end 16. Preferably the tube 12 extends through a transparent housing 18 so that the first end 14 of the tube 12 extends outwardly from one side of the housing 18 while the second end 16 of the tube 12 extends outwardly from the opposite side of the housing 18.

Still referring to FIG. 1, an inflatable bladder 20 has its inlet 22 fluidly connected to the second end 16 of the tube 12. Thus, a person exhaling breath into the first end 14 of the tube 12 inflates the bladder 20 as shown in phantom line in FIG. 2. Consequently, the inflatable bladder 20 forms an exhalation volume indicating means with the size of the bladder 20 increasing proportionally with the volume of the exhaled breath.

An alcohol reactant substance 24 is contained within the interior of the tube 12 so that exhaled breath passing through the tube 12 contacts the alcohol reactant substance 24. This alcohol reactant substance 24 changes color when the alcohol content of the breath exhaled through the tube 12 exceeds a predetermined amount, such as 0.10 percent.

Preferably the alcohol reactant substance comprises a mixture of potassium dichlorate, sulphuric acid and silver nitrate. Furthermore, the respective portions of these components are 2.5 w/w % potassium dichlorate, about 50 w/w % sulphuric acid and the balance silver nitrate. This alcohol reactant substance is also supported on the interior sides of the tube 12 by a crystallized silica gel in which the potassium dichlorate, silver nitrate and sulphuric acid are dispersed and supported.

A screen 26 is preferably disposed within the interior of the tube 12 on opposite ends of the alcohol reactant substance 24. These screens 26 allow the exhaled breath to flow freely through the tube 12 while preventing dislodgement of the alcohol reactant substance 24.

Figure 2:
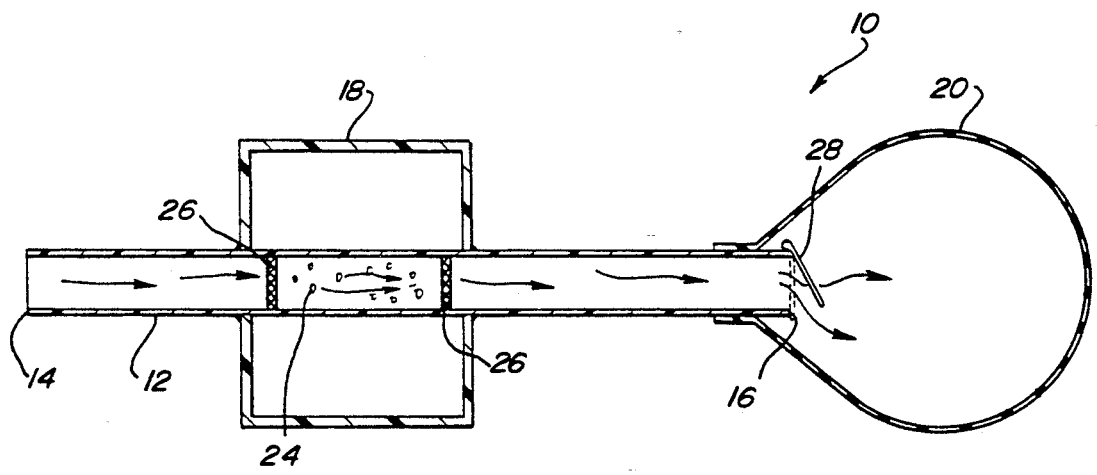
FIG. 2 is a side diagrammatic view illustrating the preferred embodiment of the present invention.

As best shown in FIG. 2, a one way valve 28 is fluidly connected in series with the second end 16 of the tube 12. This one way valve 28 is preferably a flap disposed across the end 16 of the tube 12 so that air flow into the bladder 20 is freely permitted while, conversely, the flap valve 28 prevents reverse flow from the bladder 20 in through the tube 12.

The transparent housing 18 protects the tube 12, as well as the alcohol reactant substance, from breakage. Furthermore, in the event of breakage of the tube 12, the alcohol reactant substance 24 is harmlessly contained within the interior of the container 18.

In operation, the person under test blows into the first end of the tube 14, through the tube as shown by the arrows in FIG. 2 and thus inflates the bladder 20. In doing so, the exhaled breath comes in contact with the alcohol reactant substance 24 contained within the interior of the tube 12.

After sufficient breath has been exhaled, as determined by the size of the inflated bladder 20, the color of the alcohol reactant substance 24 is examined. A change in color, e.g. to a brown color, indicates a breath alcohol content in excess of a predetermined amount, e.g. 0.08%–0.1%.

From the foregoing, it can be seen that the present invention provides a simple, inexpensive and disposable breath alcohol tester. Having described my invention, however, many modifications thereto will become apparent to those skilled in the art to which it pertains without deviation from the spirit of the invention as defined by the scope of the appended claims.

I claim:

1. A breath alcohol tester comprising:
   an elongated tube having a first end and a second end, at least portion of said tube being transparent,
   an alcohol reactant substance contained within the interior of said tube,
   an exhalation volume indicating means fluidly connected to said second end of said tube,
   wherein said alcohol reactant substance comprises a mixture of potassium dichlorate, sulphuric acid and silver nitrate.

2. The invention as defined in claim 1 wherein said exhalation volume indicating means comprises an inflatable bladder.

3. The invention as defined in claim 1 and comprising a one way valve in fluid communication with said second end of said tube, said one way valve allowing fluid flow only into said exhalation volume indicating means.

4. The invention as defined in claim 3 wherein said valve comprises a pivotal flap which overlies said one end of said tube.

5. The invention as defined in claim 1 wherein said alcohol reactant substance comprises about 0.5 w/w % potassium dichlorate, about 50 w/w % sulphuric acid and about 47.5 w/w % silver nitrate.

6. The invention as defined in claim 1 wherein said alcohol reactant substance comprises a silica gel.

7. The invention as defined in claim 1 wherein said alcohol reactant substance changes color in the presence of alcohol.

8. The invention as defined in claim 6 wherein said gel supports said potassium dichlorate, said sulphuric acid and said silver nitrate.

9. The invention as defined in claim 1 and comprising a transparent housing secured around said tube.

* * * * *